US008747409B2

(12) United States Patent
Ichelmann et al.

(10) Patent No.: US 8,747,409 B2
(45) Date of Patent: Jun. 10, 2014

(54) SURGICAL INSTRUMENT FOR POSITIONING A SPINAL ROD (75) Inventors: Bruno Ichelmann, Limoges (FR); Gilles Larroque-Lahitette, Lagor (FR)

(73) Assignee: Zimmer Spine, Bordeaux (FR)

( * ) Notice: Subject to any disclaimer, the term of this patent is extended or adjusted under 35 U.S.C. 154(b) by 144 days.

(21) Appl. No.: 13/310,017

(22) Filed: Dec. 2, 2011

(65) Prior Publication Data
US 2012/0143269 A1  Jun. 7, 2012

(30) Foreign Application Priority Data
Dec. 3, 2010  (EP) ..................... 10306349

(51) Int. Cl.
*A61B 17/56* (2006.01)
(52) U.S. Cl.
USPC .......................................... 606/86 R; 606/99
(58) Field of Classification Search
USPC ......................... 606/86 R, 99, 265
See application file for complete search history.

(56) References Cited

U.S. PATENT DOCUMENTS

| 3,039,339 A | * | 6/1962 | Hanson ...................... 81/177.2 |
| 5,658,272 A | * | 8/1997 | Hasson ........................ 606/1 |
| 2007/0270867 A1 | | 11/2007 | Miller et al. |
| 2007/0270869 A1 | * | 11/2007 | Young et al. .................... 606/86 |
| 2008/0045956 A1 | | 2/2008 | Songer et al. |

FOREIGN PATENT DOCUMENTS

| WO | WO2009/158707 A1 | 12/2009 |
| WO | WO2010/054079 A2 | 5/2010 |

OTHER PUBLICATIONS

Extended European Search Report issued for European Patent Application No. EP 10 306 349.1, mailed Aug. 30, 2011, 3 pgs.

* cited by examiner

*Primary Examiner* — Christian Sevilla
(74) *Attorney, Agent, or Firm* — Seager, Tufte & Wickhem, LLC (57) ABSTRACT A surgical instrument including an elongate member, a support for engaging a rod receiving element, and a connection between the elongate member and the support. This connection comprises a pivotal articulation, and the elongate member is connected to the support via the pivotal articulation so as to be able to pivot independently around at least two perpendicular axes. The elongate member is also longitudinally movable with respect to the support. The elongate member has, at a first end, a device for holding a rod.

9 Claims, 10 Drawing Sheets

SURGICAL INSTRUMENT FOR POSITIONING A SPINAL ROD

CROSS-REFERENCE TO RELATED APPLICATIONS

The present application claims the benefit of European Patent Application No. 10306349.1, filed on Dec. 3, 2010.

TECHNICAL FIELD

The systems devices and methods in the present disclosure relate to a surgical instrument and in particular to a surgical instrument for introducing a rod in a rod receiving element of an orthopaedic device.

One field of application for this instrument is the assembly of orthopaedic devices for holding bones in a relative position, for example to aid in the healing of breaks or the positioning of bones in the treatment of spinal deformities or spinal degenerative diseases or trauma diseases, or otherwise to correct abnormal curvatures of the spine. Other bone deficiencies and abnormalities may also benefit from embodiments of the invention.

BACKGROUND

The spine is formed of superposed vertebrae, normally aligned along a vertebral axis, from the lumbar vertebrae to the cervical vertebrae, each having a posterior wall from which projects a spinous process and two lateral edges from the walls of which there project ribs and/or transverse processes and/or lamina. If the spine of a person has abnormal curvature, the vertebrae are typically inclined relative to one another and relative to the vertebral axis.

In order to straighten the vertebral column as a remedy for this situation, the lateral edges of the vertebrae on the concave side can be moved away from one another and supported at distances from one another substantially equivalent to the distances between the lateral edges on the other side. Devices known in the art for holding the vertebrae relative to one another include rods that are held by rod-receiving elements attached to the vertebrae, for example using screws, hooks, or flexible ligatures.

The assembly of the rods to the rod receiving elements is normally carried out, in the operating theatre, after the rod-receiving elements have been surgically anchored to an osseous structure of the patient. It is therefore a delicate operation requiring significant skill. In order to facilitate it, it is known in the art to use specialised surgical instruments, such as a so-called persuader, which is a surgical instrument comprising an elongate member with, at a first end, a device for holding the rod substantially transversally to the elongate member. While such a persuader is adequate for pushing the rod in the direction of the elongate member, it is less useful for translating the rod laterally, that is, perpendicularly to both this elongate member and the rod. This is a significant drawback in particular when the rod-receiving elements are not top- but side-loading, and therefore require a lateral translation of the rod to properly engage it.

Another surgical instrument has been proposed, which is sold by Medtronic under the trade name CD Horizon® Legacy™ 5.5 Translator Rod Pusher, and comprises comprising an elongate member with a support for engaging a rod receiving element, and a hinged connection between the support and the elongate member. The elongate member comprises, at its distal end, a device for holding a rod to be introduced into the rod-receiving element.

SUMMARY

A first object of the disclosure is that of providing a surgical instrument which allows an easier and more accurate and reliable lateral positioning of the rod, in particular with respect to the rod-receiving element.

Accordingly, in at least one illustrative embodiment, a surgical instrument according to the present disclosure comprises an elongate member with, at a distal first end, a device for holding a rod, a support for engaging a rod receiving element, and a connection between the support and the elongate member, the connection comprising a pivotal articulation, wherein the elongate member is connected to the support via the pivotal articulation so as to be able to pivot independently around at least two non-coincident, and in particular perpendicular axes, and is also movable along its longitudinal axis with respect to the support.

Consequently, the support is freely orientable with respect to the rod-receiving element, facilitating its use and simplifying the assembly of the orthopaedic device.

In some embodiments, the support comprises pliers for grasping the rod receiving element at a distal end of the pliers. As a result, the support can be secured in all directions with respect to the rod-receiving element, facilitating even more its use and allowing the user to translate the rod in various directions without the concerning of losing its support on the rod-receiving element.

In particular, the pliers may be biased towards a closed position, further ensuring their grasp on the rod-receiving element.

In some exemplary embodiments, two arms of the pliers converge towards the distal end of the pliers, forming a tapering passage between them so that, in use, the rod is embraced between these two arms of the pliers and centered towards the rod receiving element when it is pushed distally by the elongate element.

In further exemplary embodiments, the articulation releasably connects the elongate member to the support, in particular via a releasable form-locking connector, such as, for example, releasable form-locking connector comprises a sliding bolt biased towards a closed position in which the form-locking connector is engaged, possibly with a push button for sliding the bolt from the closed position to an open position in which the form-locking connector is disengaged. Alternatively, the releasable form-locking connector may comprise a rotating lock. The elongate element can thus be eventually released from its support, on a specific user command, for further flexibility in its use.

Within the context of the present specification, it must be understood that by "independently pivotable around at least two non-coincident, and in particular perpendicular axes", it is not meant that the articulation necessarily comprises two distinct physical axles, as in a Cardan joint. In particular, in at least some embodiments, these two degrees of freedom in rotation of the articulation are provided in a particularly simple and reliable manner by a ball-and-socket joint. In particular, the articulation may further comprise an inner screw thread within a through hole in a ball element of the ball-and-socket joint, the inner screw thread being engaged with an outer screw thread of the elongated member, and the ball-and-socket joint being lockable in rotation in the longitudinal axis of the elongated member, in particular by a longitudinal load in a direction of the axis. The longitudinal motion of the elongated member can thus be actuated, through the screw connection, by a relative rotation of the elongated member around its longitudinal axis. To actuate this rotation, the elongate member may in particular comprise a handle at a second end opposite to the first end.

In some of these embodiments, the inner screw thread is formed in an inner surface of a tube held within the through hole in the ball element. The length of the inner screw thread in engagement with the outer screw thread of the elongated member can therefore be increased, reducing the friction between the screw threads, in particular while the elongated member is being pushed to lock the ball-and-socket joint. The reliability and usability of the surgical instrument is thus improved.

Another object of the disclosure is that of providing a method for introducing a rod into a rod receiving element of an orthopaedic device, wherein the rod is held at a first end of an elongate member which is connected to a support via an articulation, the support is fixed to the rod receiving element, the elongate member is pivoted at the articulation and moved longitudinally with respect to the support in order to insert the rod into the rod receiving element.

The above summary of some example embodiments is not intended to describe each disclosed embodiment or every implementation of these embodiments. In particular, selected features of any illustrative embodiment or combination of embodiments within this specification may be incorporated into an additional embodiment unless clearly stated to the contrary.

BRIEF DESCRIPTION OF THE DRAWINGS

The disclosure may be more completely understood in consideration of the following detailed description of an embodiment in connection with the accompanying drawings, in which.

While the embodiments are amenable to various modifications and alternative forms, specifics thereof have been shown by way of example in the drawings and will be described in detail. It should be understood, however, that the intention is not to limit aspects of the invention to the particular embodiment described. On the contrary, the intention is to cover all modifications, equivalents, and alternatives falling within the scope of the invention.

DETAILED DESCRIPTION

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

A bone fixing system comprising at least one rod linking a plurality of rod receiving elements may be installed in a patient to hold or fix one structure in a selected relation with one or more other structures. As used herein, the term structure may refer to bones, portions of bones, or bone implants, as well as rods, elongated members, plates, or other implanted man-made devices. Such a bone fixing system may be installed using a minimally invasive surgery (MIS) procedure.

Such bone fixing systems are useful in repairing broken bones, correcting curvatures of the spine and for other surgical procedures that hold structures (e.g., bones) in a fixed relative position. They can be particularly useful for minimally invasive surgery (MIS) procedures, which can reduce trauma to soft tissue due to the relatively small incision made in a patient. For example, a surgical procedure may be performed through a 2 cm to 4 cm incision formed in the skin of the patient. Dilators, a targeting needle, and/or a tissue wedge may be used to provide access to structures without the need to form a larger incision with a scalpel through muscle and other tissue. A minimally invasive surgery (MIS) procedure may reduce an amount of postoperative pain felt by a patient as compared to invasive procedures. A minimally invasive procedure may also reduce recovery time for the patient as compared to invasive procedures. In some embodiments, the natural flexibility of skin and soft tissue may be used to limit the length and/or depth of an incision or incisions needed during the procedure. Minimally invasive procedures may provide limited direct visibility in vivo.

Such bone fixing systems may be used to correct problems due to spinal injury, deformity, or disease. For example, various bone fixing systems of this type may be used from the C1 vertebra to the sacrum to correct spinal problems. For example, a bone fixing system may be implanted posterior to the spine to maintain distraction between adjacent vertebral bodies in a lumbar portion of the spine. It may be useful for holding tendons, bones, or muscles during the healing process and may be implanted using MIS procedures and thus it is in this context that embodiments of the disclosure may be described. It will be appreciated, however, that bone fixing systems of this type may be applicable for stabilizing other areas of the body.

During surgery, at least some of the rod-receiving elements are first anchored to the underlying structure first, and then receive the rod. Maneuvering the rod, however, especially during MIS, is difficult and will often require a specific surgical instrument.

Components of surgical instruments in accordance with the disclosure may be made of materials including, but not limited to, titanium, titanium alloys, stainless steel, ceramics, and/or polymers. Some components of a surgical instrument may be autoclaved and/or chemically sterilized. Components that may not be autoclaved and/or chemically sterilized may be made of sterile materials. Components made of sterile materials can be used with other sterile components during assembly of a surgical instrument and of a bone fixing system.

Figure 1:
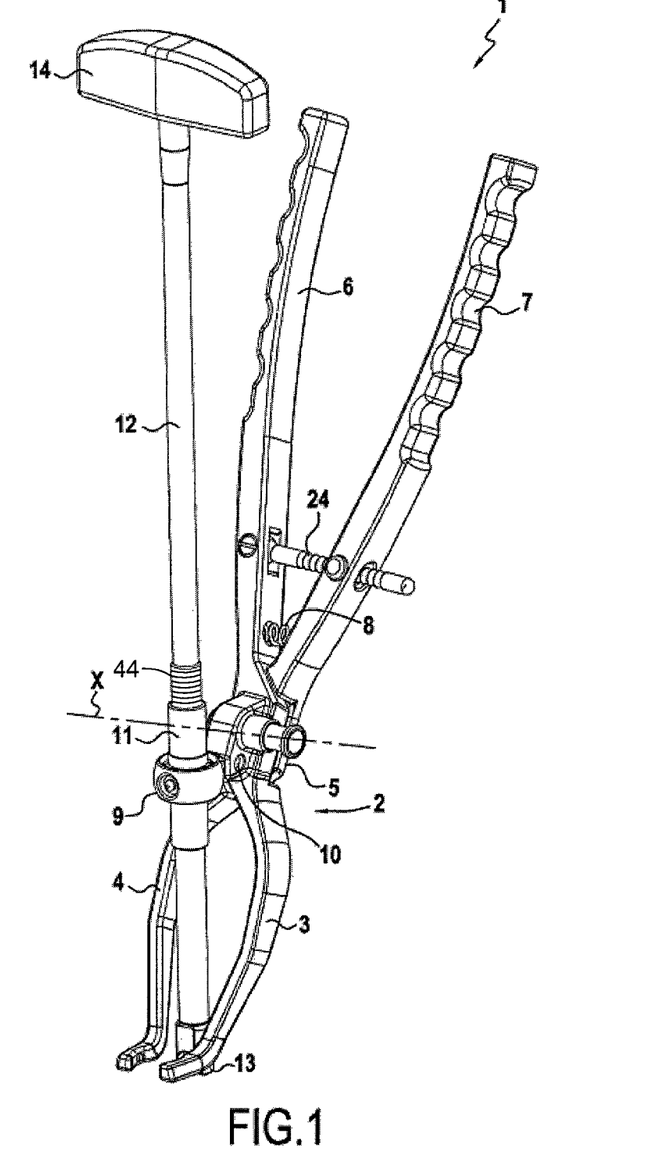
FIG. 1 depicts a perspective view of a surgical instrument according to an embodiment of the invention.
Figures 2, 3:
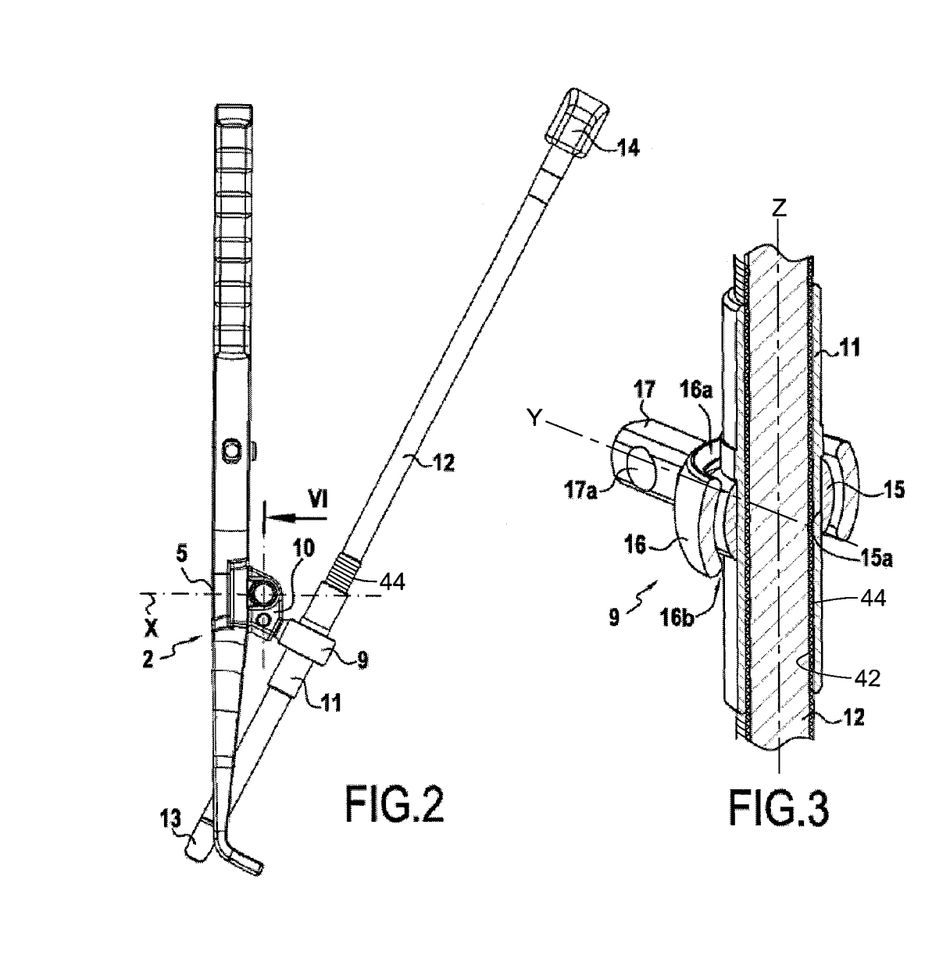
FIG. 2 depicts a side view of the surgical instrument of FIG. 1.
FIG. 3 depicts a cutaway view of a ball-and-socket articulation of the surgical instrument of FIG. 1.

An embodiment of a surgical instrument 1 according to the invention is illustrated in FIGS. 1 and 2. This surgical instrument 1 comprises pliers 2 with two arms 3, 4 connected by a hinge 5 with a hinge axis X. Each arm 3, 4 is prolonged beyond the hinge 5 by a handle 6, 7. A coil spring 8 between the handles 6, 7 biases the handles 6, 7 apart from each other, and the arms 3, 4 towards each other and to a closed position of the pliers 2, while a rack 24 can be used to lock the handles 6, 7, and therefore the arms 3, 4 at any one of a plurality of predetermined angular positions with respect to each other. The handles 6, 7 allow a user to open the pliers by unlocking the rack 24 and pushing the handles 6, 7 towards each other. A ball-and-socket articulation 9 is connected to the pliers 2 over a releasable connector 10. The ball-and-socket articulation 9 holds an internally screw-threaded tube 11 which is thus rotatable, with respect to the pliers 2, around the center of the ball-and-socket articulation 9. The surgical instrument also comprises an externally screw-threaded elongate member 12 with a rod holder 13 at a distal end and a handle 14 at a proximal end, wherein the screw thread 44 of the elongate member 12 is in engagement with the screw thread 42 of the tube 11. In some examples, rod holder 13 is connected to elongate member 12 by pivotal and/or rotatable connection 46.

FIG. 3 illustrates the ball-and-socket articulation 9 with the internally screw-threaded tube 11. The tube 11 is press-fit within an orifice 15a through the ball element 15 of the ball-and-socket articulation 9. A square-section shaft 17 with a transversal orifice 17a protrudes from one side of the annular socket 16 to provide the connection with the releasable connector 10. The friction between the ball element 15 and the socket 16 is such that, while the ball is normally freely rotatable within the socket 16, it can be frictionally locked by an axial load in the axis Z of the tube 11, as may be exerted by a user pushing on the elongate member 12 through the handle 14. Therefore, the elongate element 12 can normally be tilted around the two axes X, Y of the articulation 9 which are orthogonal to Z, but also advanced or retreated, along axis Z, with respect to the articulation 9, by a combined axial load and rotation exerted through the handle 14 at its proximal end.

Figure 4:
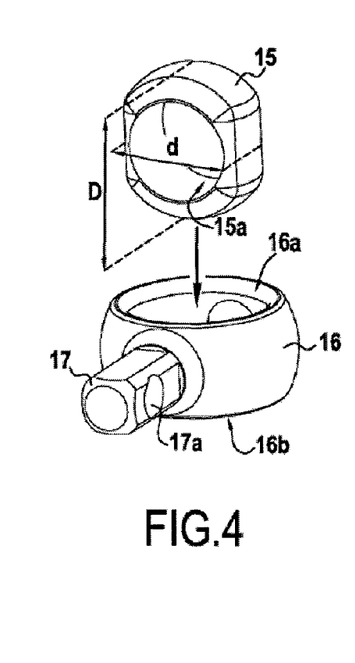
FIGS. 4 and 5 show two steps of the assembly of the ball-and-socket articulation of FIG. 2.
Figure 5:
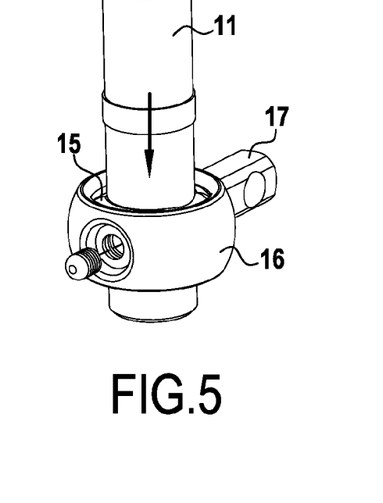

FIGS. 4 and 5 illustrate the assembly of the ball-and-socket articulation 9. Because of the part-spherical shape of the socket 16, its top and bottom openings 16a, 16b are narrower than an outer diameter D of the ball element 15. To be able to insert the ball element 15 into the socket 16, the ball element 15 presents a narrower width d in a plane perpendicular to the orifice 15a. Once the ball element 15 is inserted into the socket 16 as shown in FIG. 4, it can be tilted to align the orifice 15a with the top and bottom openings 16a, 16b of the socket 16. The screw-threaded tube 11 can then be press-fit into the orifice 15a.

Figure 6:
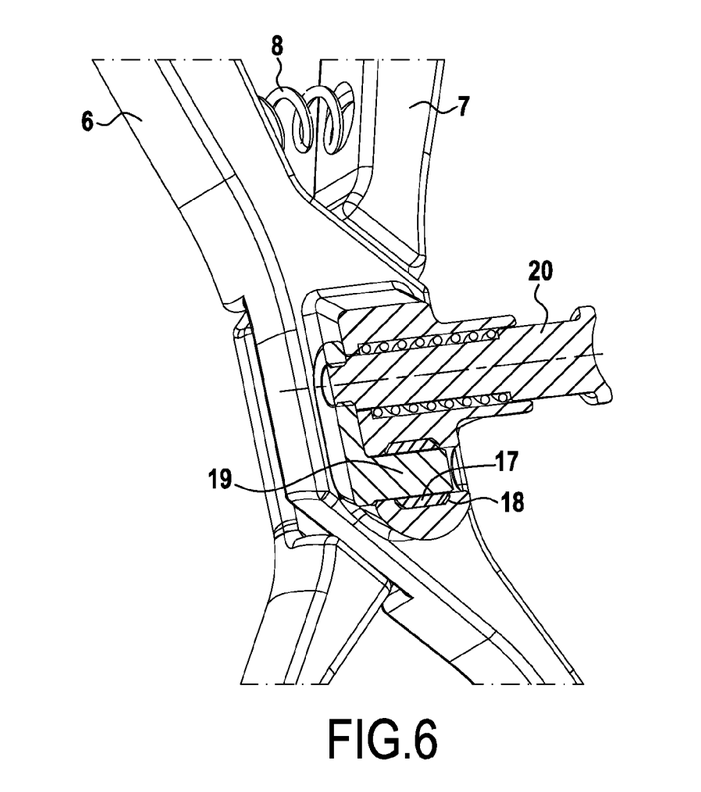
FIG. 6 depicts a transversal section, along line V-V of FIG. 1, of a releasable connection of the ball-and-socket articulation to pliers also forming part of the surgical instrument of FIG. 1.
Figure 7:
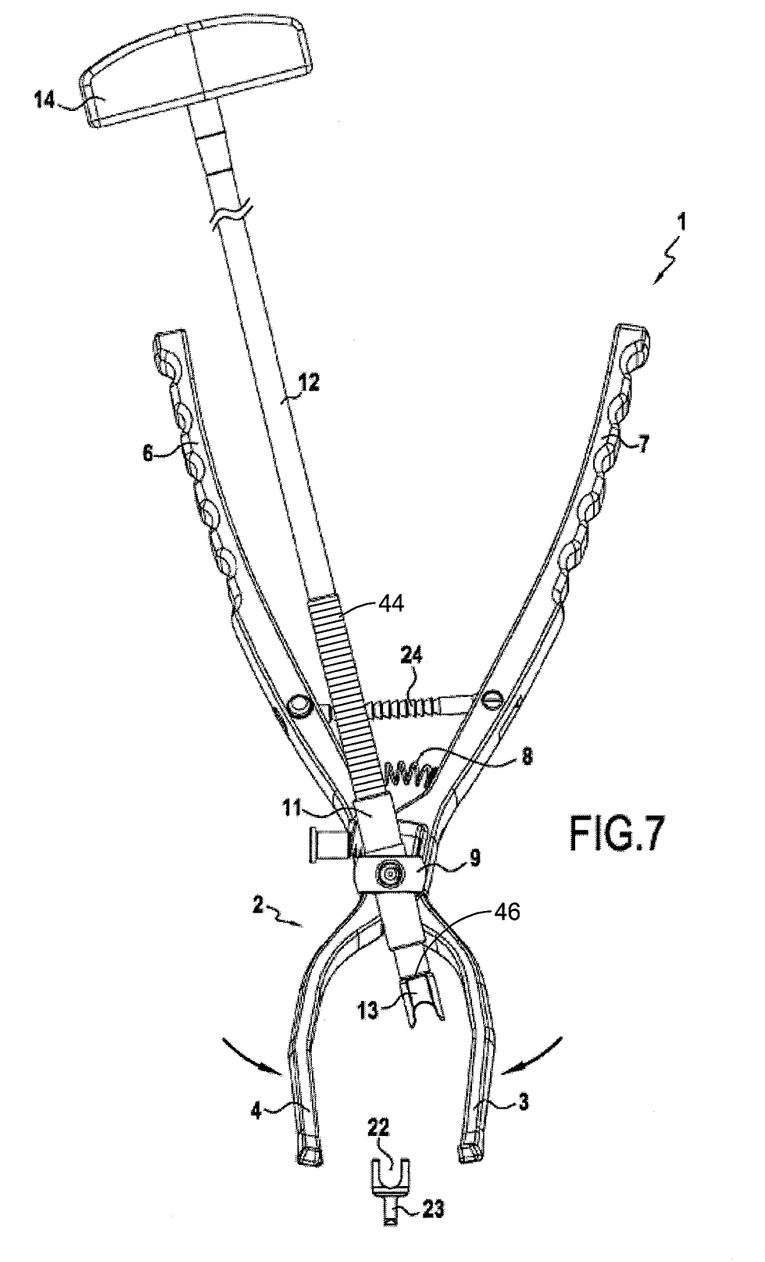
FIGS. 7, 8, 9 and 10 show four stages in an example embodiment of a first method for using the surgical instrument of FIG. 1.

FIG. 6 shows the releasable connector 10 of the articulation 9 to the pliers 2. The shaft 17 is received in a complementary recess 18, wherein it is held by a sliding bolt 19 going through the orifice 17a. The bolt 19 is coupled to a spring-loaded push-button 20, which can be pushed to disengage the pin 19 from the orifice 17a and so release the articulation 9 from the pliers 2.

Figure 8:
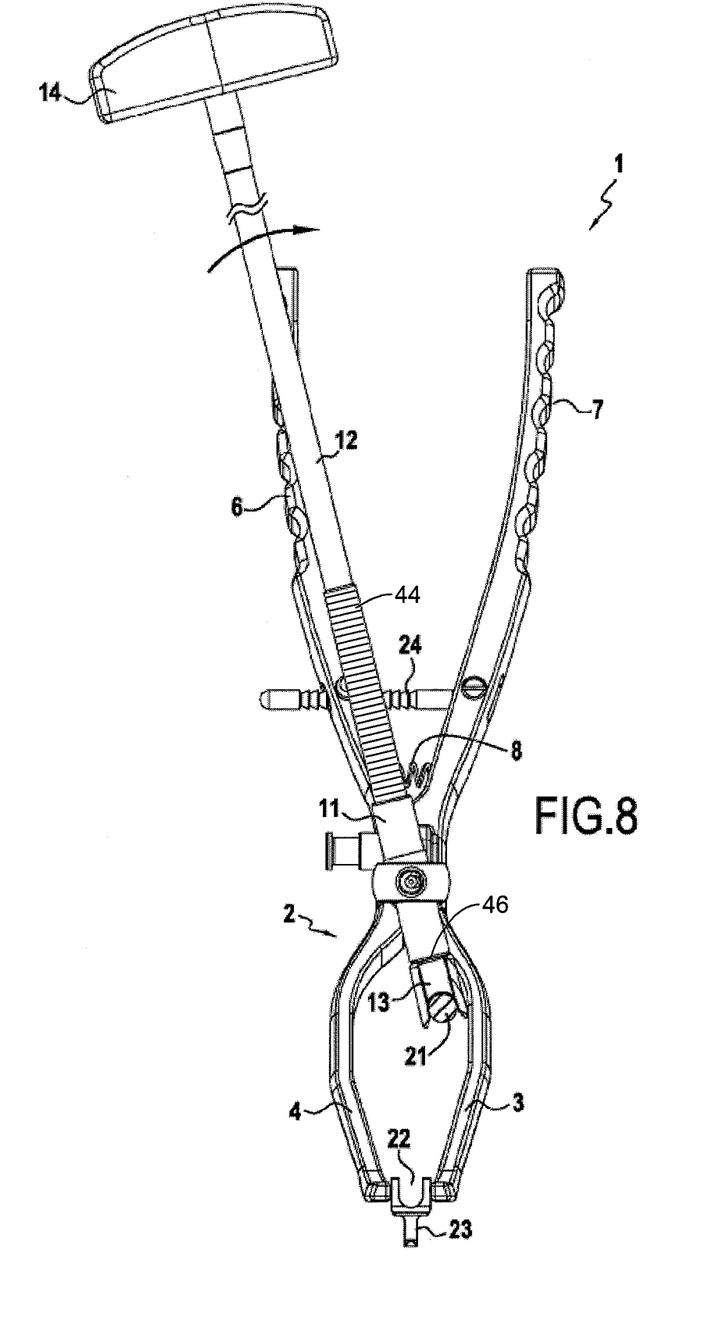
Figure 9:
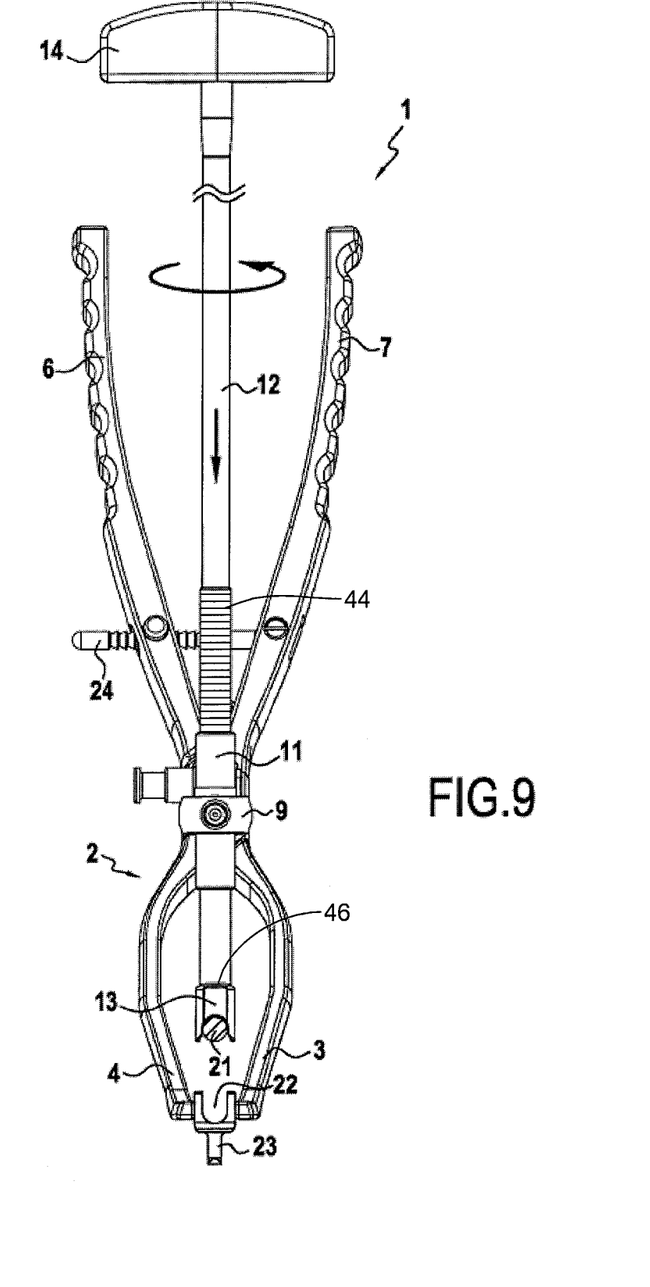
Figure 10:
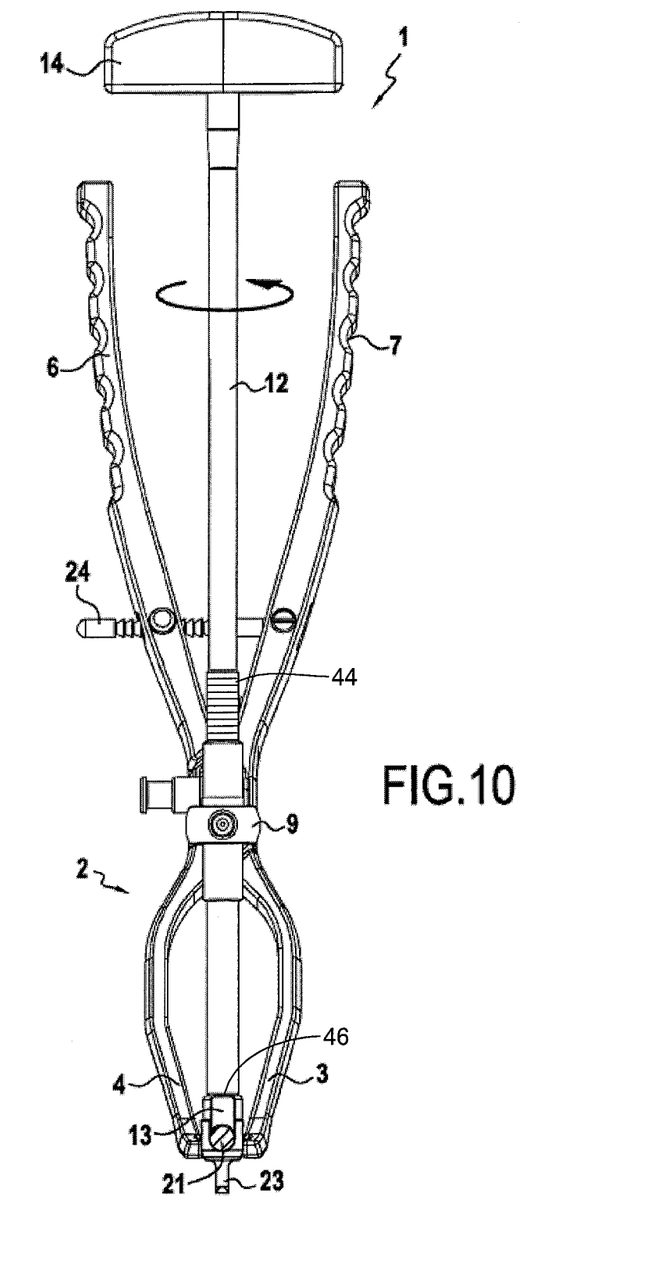

FIGS. 7 to 10 illustrate the use of the surgical instrument 1 to bring a rod 21 into a top-loading receiving portion 22 of a rod receiving element 23 anchored to an osseous structure in a patient. In a first step illustrated in FIG. 7, the operator engages the rod receiving element 23 with the pliers 2, locking the arms 3, 4 with the ratchet 24. He can then engage the rod 21 with the rod holder 13 and tilt the elongate member 12 around the articulation 9, as shown in FIG. 8, until aligning the rod 21 with the receiving portion 22. From this position, as shown in FIG. 9, simultaneously pushing and rotating the handle 14 will push the rod 21 downwards into the receiving portion 22. With the rod 21 in the receiving portion 22, as shown in FIG. 10, the elongate member 12 can still be tilted around the articulation 9 to adjust the orientation of the rod 21.

Figure 11:
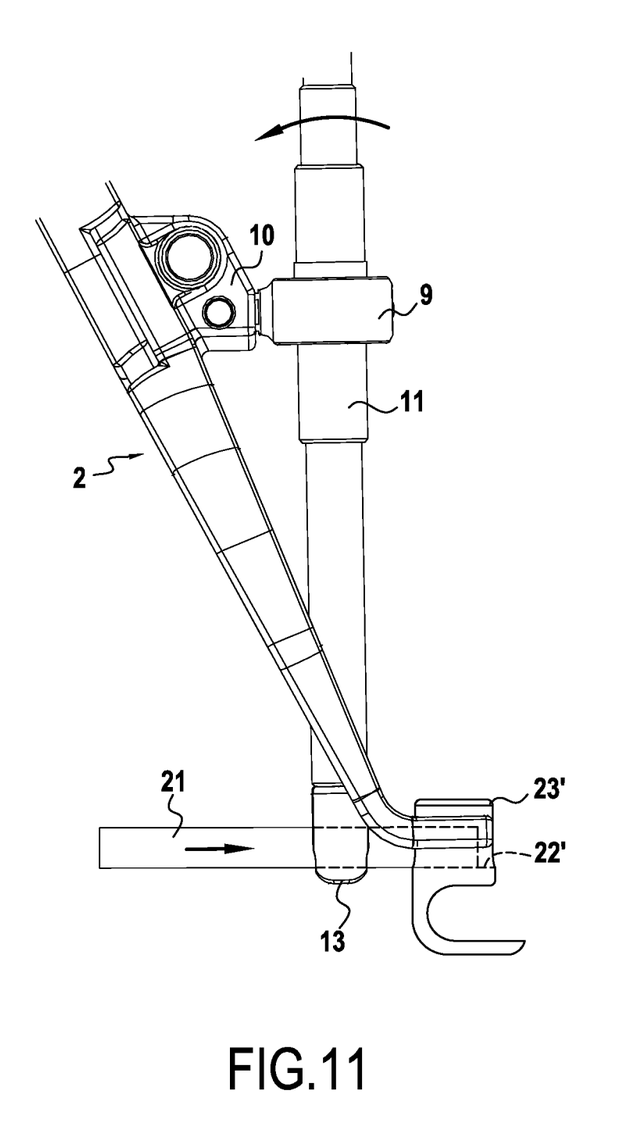
FIG. 11 shows an example embodiment of a second method for using the surgical instrument of FIG. 1.

While the method illustrated in FIGS. 7 to 10 applies to a rod receiving element 23 with a top-loading receiving portion 22, this surgical instrument 1 can also be particularly useful for side-loading rods into rod receiving elements 23. In this case, after engaging the rod 21 with the rod holder 13 and the rod receiving element 23 with the pliers 2, locking the arms 3, 4 with the rack 24, and maneuvering the elongate member 12 to longitudinally align the rod 21 with the receiving portion 22 of the rod receiving element 23, the elongate member 12 is tilted around the articulation 9 to introduce the rod 21 longitudinally into the side-loading rod receiving element 23, as shown in FIG. 11.

Figure 12:
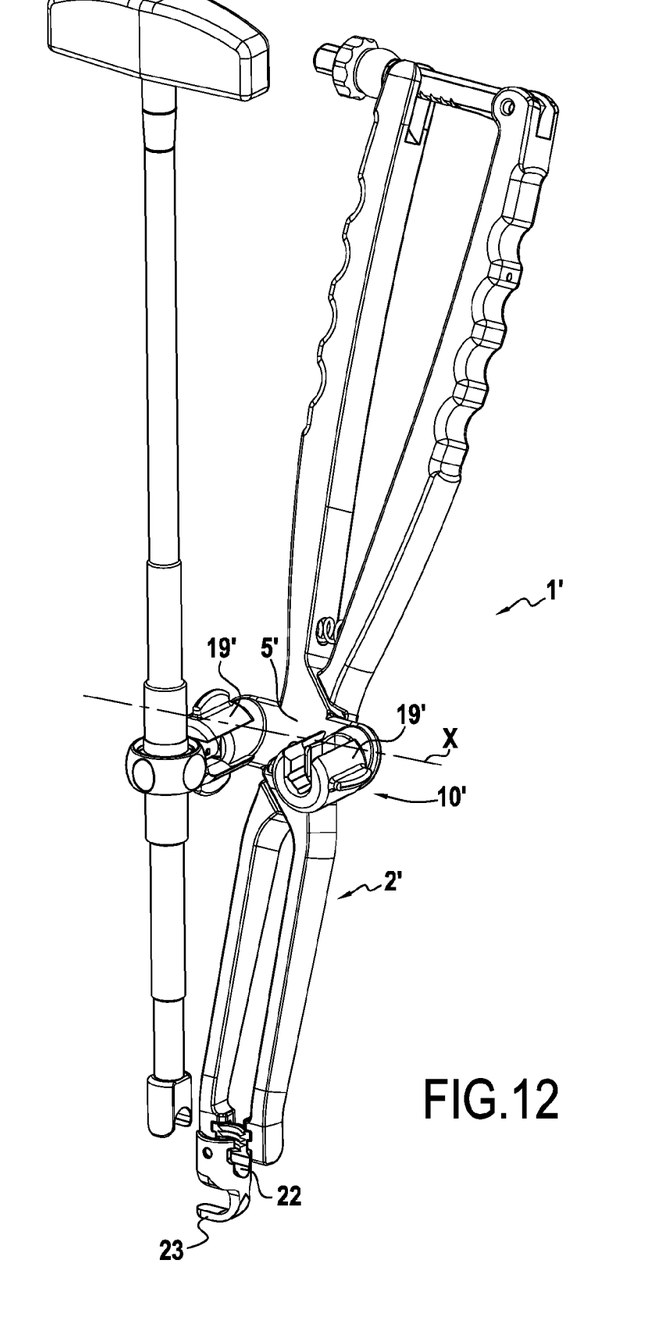
FIG. 12 depicts a perspective view of a surgical instrument according to an embodiment of the invention.

While in the methods illustrated in FIGS. 7 to 11 the pliers grasp the rod receiving element 23 substantially transversally to the receiving portion 22, the pliers may also grasp the rod receiving element 23 in a substantially parallel direction to the receiving portion 22, as shown in FIG. 12. For this, a surgical instrument 1' according to a second embodiment of the invention may be particularly advantageous, in which the releasable connector 10' is laterally offset with respect to the axis X' of the hinge 5' of the pliers 2', as shown in FIG. 12. In particular, as shown in this drawing, the surgical instrument 1' may comprise two releasable connectors 10', each one offset to one side of the axis X'.

Figure 13:
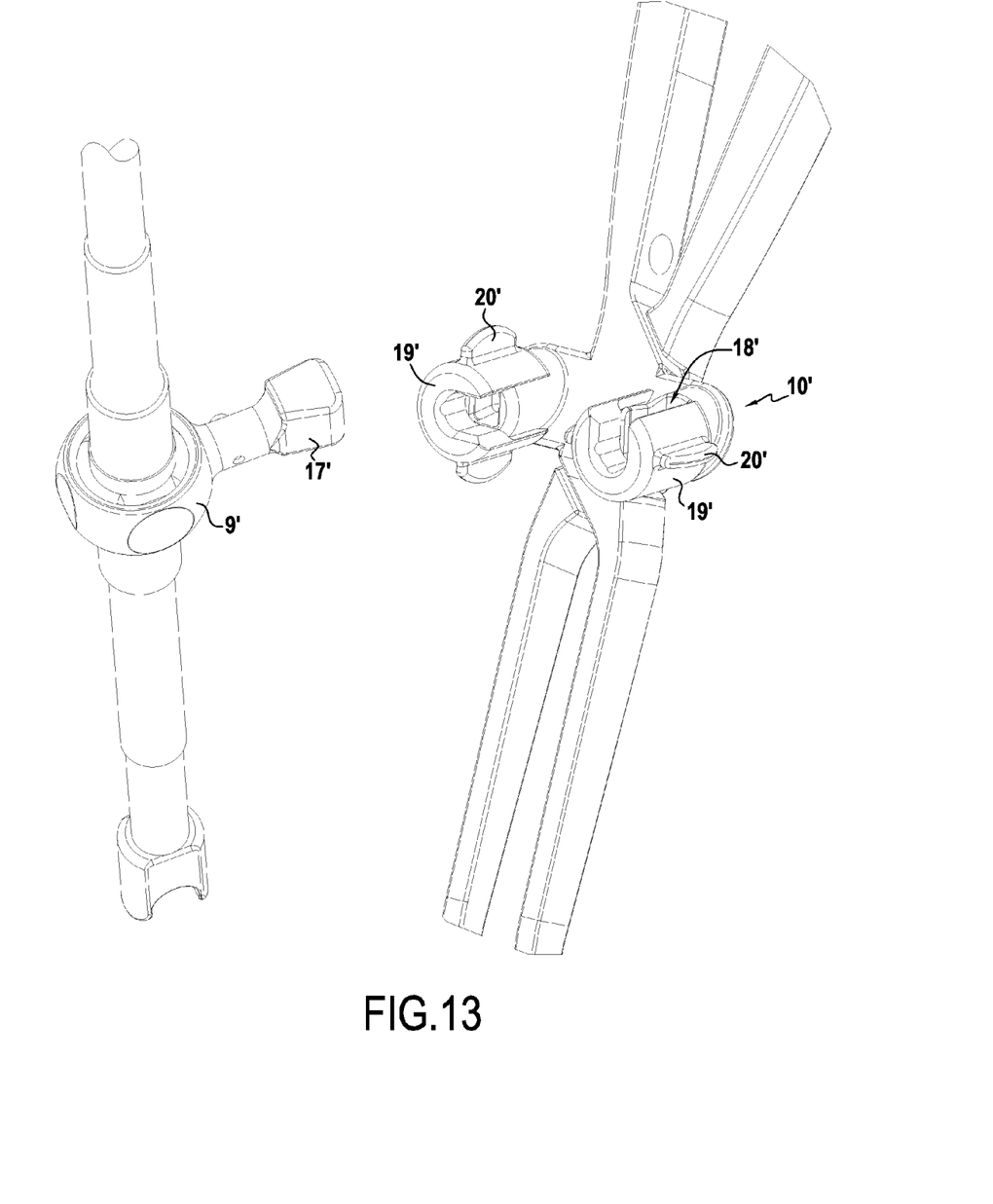
FIG. 13 shows an example embodiment of a method for using the surgical instrument of FIG. 12.

Each releasable connector 10' also differs from that of the first illustrated embodiment in that the closing member is not a sliding bolt operated by a push button, but a rotating lock 19' operated by wings 20'. As illustrated in FIG. 13, in this embodiment, in order to connect the articulation 9' to the pliers 2', a square-section protrusion 17' of the articulation 9' is introduced vertically into a complementary recess 18' within the releasable connector 10', with the rotating lock 19' in an open position, like the right-hand releasable connector 10' of FIG. 13. To lock the protrusion 17' within the recess 18', the rotating lock 19' is rotated to a closed position, like that of the left-hand releasable connector of FIG. 13. The articulation 9' is thus secured with respect to the pliers 2'. To release it again, the rotating lock 19' may then be rotated back into the open position.

Those skilled in the art will recognize that the invention may be manifested in a variety of forms other than the specific embodiment described and contemplated herein. Accordingly, departure in form and detail may be made without departing from the scope of the systems, devices and methods of the present disclosure as described in the appended claims.

The invention claimed is:

1. A surgical instrument, comprising:
   an elongate member with, at a distal first end, a device for holding a rod;
   a support for holding a rod receiving element, wherein the support comprises pliers for grasping the rod receiving element at a distal end of the pliers; and
   a connection between the support and the elongate member, the connection comprising a pivotal articulation,
   wherein the elongate member is connected to the support via the pivotal articulation so as to be able to pivot independently around at least two non-coincident axes and movable along a longitudinal axis with respect to the support, and wherein the pivotal articulation comprises a ball-and-socket joint and a through hole in a ball element of the ball-and-socket joint which is suitable for receiving the elongate member, and wherein the elongate member is longitudinally movable in the through hole.

2. The surgical instrument of claim 1, wherein the pivotal articulation further comprises an inner screw thread within the through hole in the ball element of the ball-and-socket joint, the inner screw thread being engaged with an outer screw thread of the elongated member, and the ball-and-socket joint being lockable in rotation in the axis of the inner and outer screw threads.

3. The surgical instrument of claim 2, wherein the inner screw thread is formed in an inner surface of a tube held within the through hole in the ball element.

4. The surgical instrument of claim 1, wherein the elongate member comprises a screw thread, the pivotal articulation comprises a complementary screw thread, and the screw thread of the elongate member is adapted for engagement with the complementary screw thread of the pivotal articulation.

5. The surgical instrument of claim 1, wherein the elongate member comprises a handle at a proximal second end opposite to the distal first end.

6. The surgical instrument of claim 1, wherein the device for holding the rod is pivotally and/or rotatably connected to the distal first end of the elongate member.

7. The surgical instrument of claim 1, wherein, in a closed position of the pliers, two arms of the pliers converge towards the distal end of the pliers, forming a tapering passage between them.

8. The surgical instrument of claim 1, wherein the connection is releasable.

9. The surgical instrument of claim 8, wherein the connection comprises a releasable form-locking connector.

\* \* \* \* \*